United States Patent
Schopf et al.

(10) Patent No.: US 7,060,096 B1
(45) Date of Patent: Jun. 13, 2006

(54) IMPLANT CONSISTING OF BONE MATERIAL

(75) Inventors: Christoph Schopf, Mohrendorf (DE); Karl Koschatzky, Erlangen (DE); Rolf-Dieter Kalas, Sohrewald (DE); Matthias Lowel, Nuremberg (DE)

(73) Assignee: Tutogen Medical GmbH, Neunkirchen am Brand (DE)

( * ) Notice: Subject to any disclaimer, the term of this patent is extended or adjusted under 35 U.S.C. 154(b) by 47 days.

(21) Appl. No.: 10/129,259

(22) PCT Filed: Oct. 30, 2000

(86) PCT No.: PCT/EP00/10672

§ 371 (c)(1),
(2), (4) Date: Jul. 10, 2002

(87) PCT Pub. No.: WO01/32110

PCT Pub. Date: May 10, 2001

(30) Foreign Application Priority Data

Nov. 3, 1999 (DE) .............................. 199 52 939

(51) Int. Cl.
*A61F 2/44* (2006.01)

(52) U.S. Cl. ................... 623/17.11; 623/17.16
(58) Field of Classification Search ........... 623/17.11, 623/17.12, 17.13, 17.14, 17.15, 17.16; 606/60, 606/61
See application file for complete search history.

(56) References Cited

U.S. PATENT DOCUMENTS

| 4,904,261 A | * | 2/1990 | Dove et al. ............. 623/17.16 |
| 5,514,180 A | | 5/1996 | Heggeness et al. ........... 623/17 |
| 5,728,159 A | * | 3/1998 | Stroever et al. ............ 623/23.5 |
| 5,861,041 A | * | 1/1999 | Tienboon ................. 623/17.16 |
| 6,143,032 A | * | 11/2000 | Schafer et al. ........... 623/17.11 |
| 6,174,311 B1 | * | 1/2001 | Branch et al. ............... 606/61 |
| 6,245,108 B1 | * | 6/2001 | Biscup .................... 623/17.11 |
| 6,296,664 B1 | * | 10/2001 | Middleton ............... 623/17.15 |
| 6,348,071 B1 | * | 2/2002 | Steffee et al. ............ 623/17.15 |
| 6,530,955 B1 | * | 3/2003 | Boyle et al. ............. 623/17.11 |
| 6,572,654 B1 | * | 6/2003 | Santilli .................... 623/17.16 |
| 6,579,318 B1 | * | 6/2003 | Varga et al. ............. 623/17.11 |

FOREIGN PATENT DOCUMENTS

| DE | 29 06 650 A1 | | 8/1980 | |
| DE | 29 06 650 C2 | | 5/1989 | |
| DE | 41 30 546 C2 | | 10/1993 | |
| DE | 42 42 889 A1 | | 6/1994 | |
| DE | 297 20 022 U1 | | 2/1998 | |
| DE | 197 51 284 A1 | | 5/1999 | |
| DE | 299 13 200 U1 | | 10/1999 | |
| EP | 0 298 235 A1 | | 1/1989 | |
| FR | 2736537 | * | 1/1997 | ............. 623/17.11 |
| WO | WO 95/10248 | | 4/1995 | |
| WO | WO99/09914 | * | 3/1999 | ............. 623/17.16 |
| WO | WO 99/09914 | | 3/1999 | |
| WO | WO 00/40179 | | 7/2000 | |

* cited by examiner

*Primary Examiner*—Pedro Philogene
(74) *Attorney, Agent, or Firm*—Gifford, Krass, Groh, Sprinkle, Anderson & Citkowski, P.C.

(57) ABSTRACT

The invention relates to a vertebral column implant for intercorporal fusion on the vertebral column, consisting of a body which consists of bone material and which is curved in the direction in which it extends longitudinally. The size of the implant is adapted to the intermediate vertebral space available between adjacent vertebrae after the intermediate vertebral body has been removed.

11 Claims, 1 Drawing Sheet

IMPLANT CONSISTING OF BONE MATERIAL

CROSS-REFERENCE TO RELATED APPLICATIONS

This application is the U.S. National Phase of PCT/EP00/10672 filed Oct. 30, 2002, which in turn claims priority of German Patent Application DE 199 52 939.6 filed Nov. 3, 1999, the contents of which are incorporated herein by reference.

FIELD OF THE INVENTION

The present invention relates to an implant for the connection of bones and in particular to a spinal column implant for the intercorporal fusion of vertebrae which is inserted between two vertebrae to be fused.

BACKGROUND OF THE INVENTION

Through the degeneration of the vertebral disc, in particular of the vertebral disc nucleus (nucleus pulposus) a loss of height in the affected vertebral disc space often comes about which is connected with a loosening of the vertebral disc annulus (annulus fibrosus) and of the ligaments. Through this, the spinal column becomes instable at this location. The result is a horizontal displaceability of the vertebral bodies relative to one another (spondylolisthesis), which leads to impairments of the nerve roots in this region and/or of the spinal cord together with the pain resulting from this. Similar symptoms can arise after a chemoenzymatic or physical (laser) disintegration of the vertebral disc nucleus (nucleolysis) for the treatment of a herniated disc (post-nucleolysis syndrome).

The principle for treating these symptoms consists in the surgical removal of the vertebral disc nucleus and the laying in or insertion respectively of one—in the region of the cervical vertebral column—or of two—in the region of the lumbar vertebral column—sufficiently stable bodies in order to restore the normal height of the vertebral disc space.

At the same time the horizontal displaceability must be prevented. This takes place either through the implant itself or through additional metal implants (instrumented fusion). These implants are subject in particular in the lumbar vertebral column to considerable forces, which can lead to the breakage of the metal implant. Therefore an attempt is made to have the intermediate vertebral insert grow together or fuse respectively as rapidly and as solidly as possible with the adjacent vertebral bodies.

Essentially two techniques are used for the treatment of patients with spinal trauma or degenerative disease of the spinal column.

1. Removal of the vertebral disc nucleus and of the cartilage at the end-plates, expansion of the intervertebral space to a normal width and insertion of a plano-parallel or horizontally slightly wedge-shaped block (Smith-Robinson technique).
2. Expansion of the vertebral disc space to normal height, drilling of a cylindrical opening which covers both vertebrae and insertion of a cylindrical dowel (Cloward technique). The dowel can in this connection either be a smooth cylinder or have the shape of a machine bolt.

A relatively new method for the intercorporal fusion at the lumber vertebral column is the posterior lumbar intercorporal fusion in a unilateral transforaminal technique. In this connection, the foramen intervertebrale of the affected segment is opened unilaterally, the vertebral disc space is removed and, for the ventral support, two titanium lattice baskets are introduced which are cut to the matching height and which are filled with bone chips. This tissue-saving method does, however, have different disadvantages. On the one hand, the sharp edges of the titanium baskets can damage the nerve roots during introduction. Furthermore, no lordosiation is possible as the baskets are practically introduced blind. Finally, only the rims of the basket are available to absorb the pressure present. The titanium makes the fusion control more difficult due to artifacts and in computer tomography. Furthermore, the implant removal in revision operations is extremely difficult.

The object of the present invention therefore lies in providing an implant for the fusion of bones which eliminates the aforesaid disadvantages.

SUMMARY OF THE INVENTION

This object is satisfied by a spinal column implant for intercorporal fusion at the spinal column consisting of a body of bone material which has a substantially rectangular or trapezoidal cross-section and which is made curved in the direction of its longitudinal extent, whereby one convexly curved side and one concavely curved side is formed, and wherein the implant is matched in size to the intervertebral space between adjacent vertebrae after the removal of the intervertebral body.

A special advantage of the spinal column implant in accordance with the invention is given by the material used which does not represent a foreign body due to its biological origin and to a special preservation. Furthermore, due to the curved design of the implant, the advantage results that it is matched to the shape of the front edge of the lumbar vertebrae and thus automatically comes into the right position on insertion.

Further advantageous embodiments of the spinal column implant in accordance with the present invention are specified in the description, the drawing and the dependent claims.

DETAILED DESCRIPTION OF THE INVENTION

The present invention will be described in the following in a purely exemplary manner with reference to embodiments of a spinal column implant in accordance with the invention and with reference to the accompanying drawings. There are shown:

DETAILED DESCRIPTION OF THE INVENTION

Figure 1:
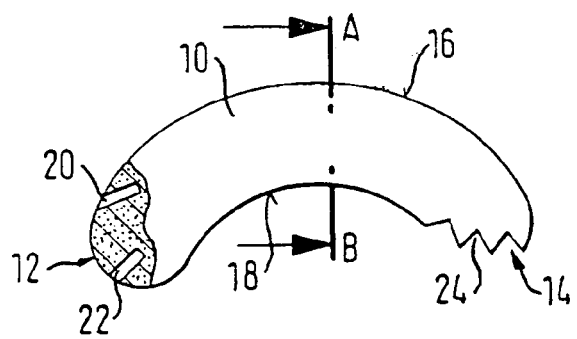
FIG. 1 is a plan view of an embodiment of a spinal column implant in accordance with the present invention.

In accordance with the invention, the body can consist of processed, preserved and sterile bone material of human origin, a so-called allograft, or of processed, preserved and sterile bone material of animal origin, a so-called xenograft.

The body can be made of solid cortical bone material or also of spongeous bone material, for example of the humerus, femur, tibia or of other bones either of deceased humans or of animals, in particular of bovine bone material, or also as a hollow body which is then filled with spongeous bone material.

In a particularly advantageous embodiment of the spinal column implant in accordance with the invention, the body has a banana-like curvature and rounded edges. Such a design of the body facilitates the application of the spinal column implant between the vertebral bodies to be fused in that the roundings avoid a canting of the implant during application. The implant is matched particularly well to the natural shape of the end plates of the vertebral bodies by the special banana shape and so offers the largest possible contact surface for the end plates. In this way, a more physiological distribution of the forces takes place, whereby pressure peaks and a subsiding of the implant into the vertebral bodies due to this are avoided. Since a correct positioning takes place automatically due to the curvature of the implant, the restoration of the physiological curvature of the spinal column—lordosis—is also possible by a trapezoidal cross-section.

It is particularly advantageous when notches or recesses are provided at the body which make possible the taking along of loosely introduced bone powder into the intervertebral space. In this way, bone powder can automatically be introduced into the concavely shaped region of the implant during insertion of the implant into the intervertebral space.

In accordance with a further aspect of the present invention, reception openings are designed at one or more sides of the body as drillings with a thread of a depth of preferably 3 mm. Application tools provided with a matching thread can then be screwed into these tapped drillings in order to insert the implant in an accurate position between the vertebrae to be fused.

As the material for the spinal column implant in accordance with the present invention, a suitable allogenic or xenogenic bone material is processed in such a manner that it is preserved, is capable of storage, is sterile and can be used in accordance with its purpose. The preservation of the bone material can for example take place by means of freeze drying. Another preferred method for the production of the bone material is a processing through preferably solvent dehydration of native bone material by means of an organic solvent which is miscible with water, e.g. methanol, ethanol, propanol, isopropanol, acetone, methyl ethyl ketone or mixtures of these solvents. The preservation and sterilization of the bone material in accordance with this method is also a subject matter of the patent DE 29 06 650, the contents of which are taken up into the disclosure of the present application through this reference.

This method serves for the production of transplant preserves and enables a dehydration and exposure right into the fine structure of the fibrils of the bone material, so that the processed bone material has a morphological structure in a histological view which is very similar to that of the natural bone, and thus the desired properties of the bone material are retained. This method of solvent dehydration also has the advantage that a substantially lower apparatus cost and complexity is required in comparison with freeze drying.

Furthermore, the bone material can also be produced through solvent dehydration of bone material with subsequent terminal sterilization, in particular through irradiation with gamma rays. Alternatively, the spongeous bone material can be produced through aseptic processing of bone material without terminal sterilization. The starting material of the bone implant in accordance with the invention is human or animal bone of sufficient size.

To remove the antigenicity, the bone is subjected to an osmotic treatment. Furthermore, an oxidizing treatment is carried out for denaturation of soluble proteins. To optimize virus deactivation, a reduction of pH to pH 3, or a treatment with caustic soda or another substance which destroys DNA/RNA, can take place. The dehydration takes place through organic solvents, preferably acetone. The concluding sterilization takes place through high-energy radiation, preferably γ rays with a maximum dose of 25 kGy.

A bone treated in this manner maintains its natural mineral collagen bond and properties. Furthermore, a bone treated in this manner can be reworked.

In the figures the same reference symbols designate in each case the same components of the illustrated embodiments.

The embodiment of a spinal column implant in accordance with the invention illustrated in FIG. 1 comprises a body 10, which consists, for example, of cortical, diaphyseal bone material, e.g. of human origin. This body 10 is, in a plan view, substantially elongate and made curved in the direction of its longitudinal extent.

The two opposite ends 12 and 14 of the body 10 are made rounded such that overall a banana-like or also kidney-like design of the base body 10 results. The body 10 has a convexly curved surface 16 and a concavely curved surface 18 between the two ends 12 and 14.

As FIG. 1 shows, the base body has two reception openings 20, 22 for application tools in the regions of its one end 12. The reception openings 20, 22 are made as drillings whose longitudinal axes do not extend parallel to one another.

In the region of the oppositely disposed end 14, a structured design of the surface of the base body is provided in the region of the concave surface 18, preferably by notches or recesses 24 which allow the taking along of loosely added bone powder into the intervertebral space. The taking along and compacting of the bone powder during the insertion of the bone implant into the intervertebral space is ensured by the structured design of the surface provided (three notches are provided in the example shown).

Figure 2:
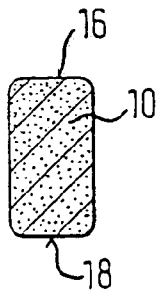
FIGS. 2 and 3 are in each case possible cross-sectional shapes of the spinal column implants in accordance with the invention.
Figure 3:
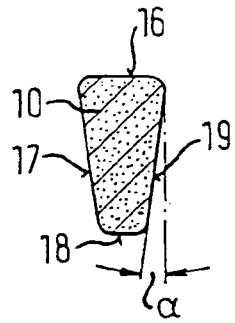

FIGS. 2 and 3 show possible cross-sectional shapes of the body 10 along the intersection line A-B of FIG. 1.

FIG. 2 shows a possible cross-sectional shape in the form of a rectangle with rounded edges. FIG. 3 shows a trapezoidal cross-sectional shape, with the obliquely extending sides of the trapezoid deviating from the rectangular shape by an angle a of approximately 3° to 6°.

As in particular FIG. 3 shows, with a trapezoidal cross-section of the implant, the obliquely extending outer sides 17, 19 can be inclined in the direction of the convex outer surface 18, i.e. in the direction of the ring center of the implant formed in the shape of a ring segment.

FIG. 1 shows a substantially symmetrical embodiment of a spinal column implant. In contrast to this, an asymmetrical shape is selected in the further embodiment shown in FIG. 4, in which the shape of the body 10' in a plan view tapers from the one end 12 in the direction of the other end 14. In other respects, the same reference numerals designate the same elements. At the same time, the cross-sectional shapes shown in FIGS. 2 and 3 can also be used in the embodiment shown in FIG. 4.

Figure 4:
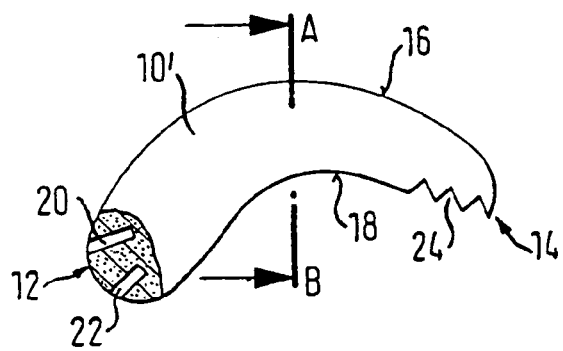
FIG. 4 is a plan view of a further embodiment of a spinal column implant in accordance with the present invention.

As FIGS. 1 and 4 show, the bodies 10, 10' have the form of a ring segment, with preferably the shape of an approximately ⅜ to ½ ring being selected. Furthermore, it can be recognized in the embodiment of FIG. 4 that the one end 12 of the body 10' is wider than the oppositely disposed end 14 in order to facilitate an insertion of the implant into the foramen intervertebrale.

Generally, the body 1 of the spinal column implant is matched in size to the pre-determined space at which the implant should be inserted. The outer dimensions of such a spinal column implant can, for example, be as follows for a lumbar application: length approximately 30 to 60 mm, width approximately 8 to 20 mm, height approximately 6 to 18 mm.

Generally, the possibility exists of forming the spinal column implant as a solid implant, for example of cortical or of spongeous bone. An alternative embodiment of the invention provides that the spinal column implant—likewise made of cortical or spongeous bone—is designed as a hollow body.

Figure 5:
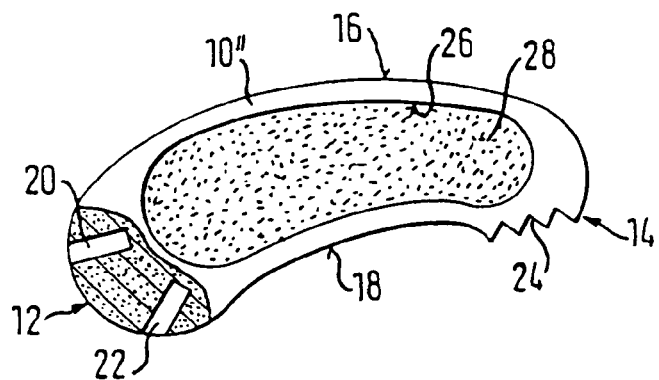
FIG. 5 is a plan view of a further embodiment of a spinal column implant in accordance with the present invention.

FIG. 5 shows such an embodiment in which the body 10" has a cavity 26 which is filled with spongeous bone 28. The cavity 26 extends substantially from the end of the reception openings 20, 22 up to and into the region of the recesses 24. In this connection, the cavity 26 is matched to the outer contour of the body 10".

The invention claimed is:

1. A spinal column implant for intercorporal fusion at the spinal column comprising a body (10, 10', 10") of bone material having a first end and an opposing second end, the body having a substantially trapezoidal cross-section and which is made curved in the direction of its longitudinal extension, whereby one convexly curved side (16) and one concavely curved side (18) is formed, and wherein the implant is matched in size to an intervertebral space present between adjacent vertebrae after removal of the intervertebral body, wherein a first and a second outer side (17, 19) connecting the one convexly curved side and the one concavely curved side are inclined in the direction of the one concavely curved side so as to form a cross-section tapering towards the concavely curved side, and wherein at least one end of the body is rounded in plan view into a semi-circular shape, wherein the first end has at least one reception opening for an application tool and the opposing second end has a plurality of notches formed across a transition between the concavely curved side and a curved surface of the second end, which allows the taking along of loosely introduced bone powder into the intervertebral space.

2. A spinal column implant in accordance with claim 1 characterized in that the body (10, 10', 10") is formed of preserved and sterile bone material of human or animal origin.

3. A spinal column implant in accordance with claim 1, characterized in that the first end and the second opposing end of the body (10, 10', 10") are rounded in plan view in a semi-circular shape.

4. A spinal column implant in accordance with claim 1, characterized in that the body (10,10', 10") has rounded edges.

5. A spinal column implant in accordance with claim 1, characterized in that the body has the form of a ring segment.

6. A spinal column implant in accordance with claim 1, characterized in that the second end (14) of the body (10') is narrower than the first end (12).

7. A spinal column implant in accordance with claim 1, characterized in that the body (10, 10', 10") is trapezoidal in cross-section having obliquely extending sides deviating from a cross-section in the form of a rectangle with rounded edges by an angle ($\alpha$) from approximately 3° to 60°.

8. A spinal column implant in accordance with claim 2, wherein said preserved and sterile bone material is bovine bone material.

9. A spinal column implant in accordance with claim 5 wherein said ring segment forms one-third to one-half a complete ring.

10. A spinal column implant in accordance with claim 1 further comprising bone powder in the at least one notch or recess.

11. A spinal column implant for intercorporal fusion at the spinal column comprising a body of bone material having a first end and an opposing second end, the body having a substantially trapezoidal cross-section and which is made curved in the direction of its longitudinal extension, whereby one convexly curved side and one concavely curved side is formed, and wherein the implant is matched in size to an intervertebral space present between adjacent vertebrae after removal of the intervertebral body, wherein a first and a second outer side connecting the one convexly curved side and the one concavely curved side are inclined in the direction of the one concavely curved side so as to form a cross-section tapering towards the concavely curved side, and wherein at least one end of the body is rounded in plan view into a semi-circular shape, wherein the body is smooth except for holes consisting of an application tool reception opening in the first end and a plurality of notches which are formed across a transition between the concavely curved side and a curved surface of the second end.

* * * * *